(12) United States Patent
Drennan

(10) Patent No.: US 10,334,905 B2
(45) Date of Patent: Jul. 2, 2019

(54) HEEL-SUSPENDING PROTECTIVE BOOT

(71) Applicant: DM Systems, Inc., Evanston, IL (US)

(72) Inventor: Denis Burke Drennan, Evanston, IL (US)

(73) Assignee: Walgreen Health Solutions, LLC, Lake Forest, IL (US)

(*) Notice: Subject to any disclaimer, the term of this patent is extended or adjusted under 35 U.S.C. 154(b) by 1389 days.

(21) Appl. No.: 14/138,455

(22) Filed: Dec. 23, 2013

(65) Prior Publication Data

US 2014/0173940 A1    Jun. 26, 2014

Related U.S. Application Data

(60) Provisional application No. 61/740,503, filed on Dec. 21, 2012, provisional application No. 61/859,336, filed on Jul. 29, 2013.

(51) Int. Cl.
  *A43B 1/00*      (2006.01)
  *A43B 7/14*      (2006.01)
  (Continued)

(52) U.S. Cl.
  CPC .......... *A43B 1/0045* (2013.01); *A43B 7/1455* (2013.01); *A43B 7/20* (2013.01);
  (Continued)

(58) Field of Classification Search
  CPC ........ A61F 5/0111; A61F 5/0195; A61F 5/01; A61F 5/0127; A61F 13/043;
  (Continued)

(56) References Cited

U.S. PATENT DOCUMENTS 4,186,738 A     2/1980  Schleicher et al.
RE33,762 E  *  12/1991  Lonardo ............... A61F 5/0113
                                                602/27

(Continued)

FOREIGN PATENT DOCUMENTS

EP         2147664         1/2010

OTHER PUBLICATIONS

Extended European Search Report dated Jun. 30, 2016.

*Primary Examiner* — Alireza Nia
*Assistant Examiner* — Rachel A Berezik
(74) *Attorney, Agent, or Firm* — Hartman Global IP Law; Gary M. Hartman; Domenica N. S. Hartman

(57) ABSTRACT

A protective boot adapted to be worn by individuals when lying in a reclining position. The boot has leg and forefoot portions that provide foot and lower leg support for a wearer while suspending the wearer's heel. The boot may include low-friction materials at an exterior surface of its leg and forefoot portions and at a continuous rim separating the exterior surface from an interior surface of the body, in which case the boot also preferably includes a system for adjustably closing an anterior opening in the forefoot portion by drawing lateral regions of the forefoot portion inward and together. The boot may additionally or alternatively include an L-shaped backplate having portions located at the leg and forefoot portions of the body and adapted to inhibit buckling of the boot within the leg and forefoot portions.

20 Claims, 3 Drawing Sheets

(51) Int. Cl.
  *A43B 7/20* (2006.01)
  *A43B 7/24* (2006.01)
  *A61F 5/01* (2006.01)
  *A43C 11/14* (2006.01)
(52) U.S. Cl.
  CPC ............ *A43B 7/24* (2013.01); *A43C 11/1493* (2013.01); *A61F 5/0195* (2013.01)
(58) Field of Classification Search
  CPC ...... A61F 13/045; A61F 13/06; A61F 13/064; A61F 5/0113; A43B 5/145; A43B 7/34; A43B 23/24; A43B 3/0078; A43B 3/166; A43B 1/0045; A43B 7/20; A43B 7/24; A43B 7/1455; A43B 5/0474; A43B 5/0492; A43B 5/04; A43B 5/0456; A43B 5/0472; A43B 5/14; A43C 11/1493; A63C 9/0805; A63C 9/0846; A63C 9/086; A63C 9/003; A63C 9/005; A63C 9/08; A63C 9/0841; A63C 9/0842; A63C 9/0847; A63C 9/0855; A63C 9/08564; B60T 8/3225; B60T 8/3685; B62K 25/08; B62K 19/38; A41D 17/02; A41D 13/0543; B60G 17/08; B60G 2202/24; B60G 2300/12; B60G 2500/10; B60G 2800/22; B60K 17/04; B62M 17/00; A41B 17/02

USPC .......................... 602/23–28, 60–62; 128/882
See application file for complete search history.

(56) References Cited

U.S. PATENT DOCUMENTS

| | | | |
|---|---|---|---|
| 5,088,481 A * | 2/1992 | Darby | A61F 13/043 36/102 |
| 5,226,245 A | 7/1993 | Lamont | |
| 5,449,339 A | 9/1995 | Drennan | |
| 5,569,174 A | 10/1996 | Varn | |
| 5,735,805 A | 4/1998 | Wasserman | |
| 5,762,622 A * | 6/1998 | Lamont | A43B 5/0415 602/27 |
| 7,294,114 B1 * | 11/2007 | Clement | A61F 5/0195 36/15 |
| 7,458,948 B2 | 12/2008 | Drennan | |
| 2005/0172517 A1 * | 8/2005 | Bledsoe | A43B 7/141 36/110 |
| 2007/0073208 A1 * | 3/2007 | Drennan | A61F 13/064 602/36 |
| 2007/0074427 A1 | 4/2007 | Ponsi et al. | |
| 2010/0022931 A1 | 1/2010 | Varn et al. | |
| 2012/0199134 A1 | 8/2012 | Carson | |

* cited by examiner

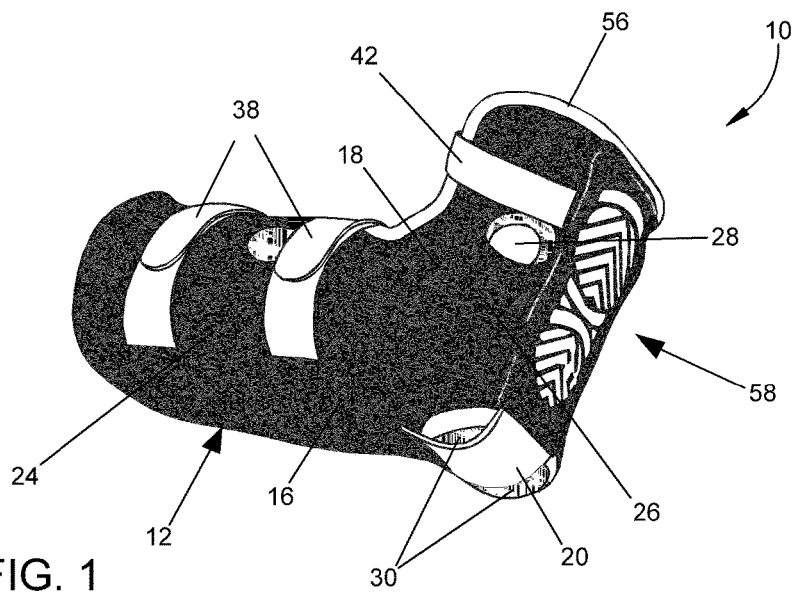
FIG. 1
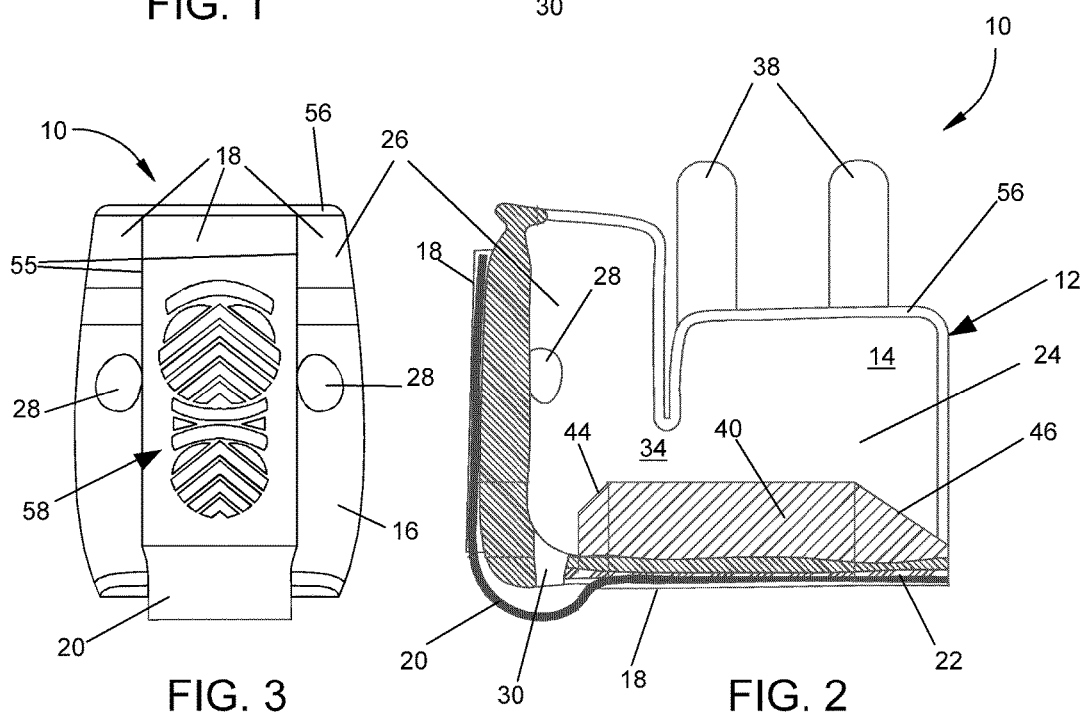
FIG. 3
FIG. 2

HEEL-SUSPENDING PROTECTIVE BOOT

CROSS REFERENCE TO RELATED APPLICATIONS

This application claims the benefit of U.S. Provisional Application No. 61/740,503, filed Dec. 21, 2012, and U.S. Provisional Application No. 61/859,336 filed Jul. 29, 2013. The contents of these prior patent applications are incorporated herein by reference.

BACKGROUND OF THE INVENTION

The present invention generally relates to devices adapted to support a leg of a person while reclining, especially patients that are bedridden and as a result are prone to bed sores, foot drop (equinus deformity foot-ankle), and other conditions that can affect the foot. More particularly, the invention is directed to a protective boot adapted to support an individual's leg at a location away from the heel such that the heel is suspended and yet the foot is properly supported, and the construction of such a boot to improve its support capabilities.

Bedridden individuals can suffer from a variety of conditions brought on by being confined in bed, especially if limited to the supine position. For example, bedridden individuals are susceptible to heel pressure ulcers, foot drop caused by pressure over the peroneal nerve, relaxation and weakening of the muscles controlling the foot, and heel cord contracture. As a preventive measure, various foot support devices have been proposed, notable examples of which are disclosed in U.S. Pat. No. 4,186,738 to Schleicher et al. and U.S. Pat. Nos. 5,449,339 and 7,458,948 to Drennan. The Drennan patents disclose heel-supporting boots commercially available from DM Systems Inc. under the name HEELIFT® Suspension Boot. The boots include a unitary body formed of a flexible and compressible foam material that defines a foot supporting portion and a leg supporting portion. The leg supporting portion is configured to wrap around the leg of an individual away from the individual's foot, and is equipped with adjustable straps that secure the boot in place on the individual's leg to inhibit movement of the boot out of a proper supportive position in the event the individual moves. The leg supporting portion supports the individual's leg from beneath to suspend the individual's foot above the surface on which the individual is reclined, with the result that heel ulcers are prevented. In addition the leg supporting portion elevates the calf relative to the bed to remove pressure from the peroneal nerve at the upper end of the leg. The foot supporting portion supports the foot by applying pressure to the sole, thereby preventing foot drop, heel cord contracture, etc. The lower surface of the boot is preferably provided with a friction-reducing element that promotes free sliding movement of the boot over the bed surface, and a stiffener is preferably provided within the boot body to inhibit buckling and folding of the boot due to friction with the bed surface.

While having beneficial elements, foot support devices in the prior art often contain high-friction materials that rub against covering bed sheets and, as a result of leg movement, can cause the device to become displaced and cause the individual's foot to shift within the device. Foot support devices may also have excess room for the foot within the device, allowing the foot to shift and rotate within the device. In addition, foam materials used in the construction of foot support devices tend to be bulky and highly deformable, with the result that portions of the device may catch on obstacles such as bed railings and wheelchair attachments. Finally, foot support devices may be heavily insulated, often unintentionally, which may be excessively warm for the wearer.

In view of the above, further improvements to foot-supporting devices and boots would be desirable, particularly with respect to inhibiting movement of the foot within the boot, easing an individual's movement under sheets, reducing bulk, reducing the likelihood that the boot will catch on obstacles, and providing better heat dissipation and ventilation.

BRIEF DESCRIPTION OF THE INVENTION

The present invention provides a protective boot adapted to support a leg of a human while reclining and further adapted to provide leg and foot support in a manner capable of reducing the risk of foot drop, heel pressure ulcers, and other foot conditions.

According to a first aspect of the invention, the boot comprises a body formed of a flexible and compressible foam material. The body has a proximal leg portion, a distal forefoot portion contiguous with and projecting from the leg portion in a transverse direction thereto, a continuous cavity defined by and within the leg and forefoot portions and being complementary in size and shape to support the lower leg of the person while supporting the foot of the person in an upright position, an anterior opening defined in the leg and forefoot portions to permit the foot and lower leg to pass therethrough into the cavity within the leg and forefoot portions, oppositely-disposed lateral regions defined by the leg portion and separated by the anterior opening, oppositely-disposed lateral regions defined by the forefoot portion and separated by the anterior opening, an interior surface defined by the leg and forefoot portions within the cavity, an exterior surface defined by the leg and forefoot portions, and a continuous rim separating the interior and exterior surfaces. The boot further comprises a cushion within the cavity within the lower leg portion for supporting the lower leg of the person and suspending the heel of the person within the cavity, a first low-friction material defining the exterior surface at the leg and forefoot portions, a second low-friction material at the continuous rim separating the interior and exterior surfaces, a first means for adjustably closing the anterior opening in the leg portion with the lateral regions of the leg portion; and a second means for adjustably closing a portion of the anterior opening in the forefoot portion with the lateral regions of the forefoot portion by drawing the lateral regions of the forefoot portion inward and toward the medial and lateral sides of the foot of the person within the forefoot portion without applying pressure to the dorsum of the foot.

A technical effect of the invention is the ability of the boot to provide greater support to the foot of an individual while also reducing friction between the boot and its surrounding environment, for example, bed coverings beneath and placed over the boot while the wearer is in bed.

Other aspects and advantages of this invention will be better appreciated from the following detailed description.

BRIEF DESCRIPTION OF THE DRAWINGS

FIG. 1 is a perspective view of heel-suspending protective boot adapted to support a human leg in accordance with an embodiment of the invention.

FIG. 2 is a cross-sectional view of the protective boot shown in FIG. 1.

FIG. 3 is an end view of the protective boot shown in FIG. 1.

DETAILED DESCRIPTION OF THE INVENTION

FIGS. 1 through 7 represent various views of a heel-suspending protective boot 10 configured to be worn on a human foot and lower leg (not shown) while the individual is in a generally supine position (reclining) on a bed or any other surface on which a person might recline while wearing the boot 10. The boot 10 is configured to support the individual's lower leg and heel in a manner that suspends the heel to avoid foot drop and relieves heel pressure to avoid heel pressure ulcers. The boot 10 is believed to provide enhancements over the function and construction of suspension boots commercially available under the name DM Systems HEELIFT®, disclosed in U.S. Pat. Nos. 5,449,339, and 7,458,948 to Drennan, of which the contents relating to the construction and composition of the suspension boot are incorporated herein by reference.

Consistent with the HEELIFT® boot, the boot 10 is adapted to support the lower leg and foot of a human with a soft foam shell 12 secured to the lower leg and foot with a closure system. The shell 12 is preferably a unitary, one-piece body formed of a flexible, compressible foam material, more preferably a material that is capable of being heated and sterilized in an autoclave or oven with limited shrinkage. A particularly preferred shell 12 is formed from a slab of open-cell non-allergenic resilient foam material such as polyurethane foam, with sufficient thickness (e.g., about 1.5 inches (about 4 cm)) to elevate an individual's foot and lower leg above a bed and provide sufficient structural support to inhibit movement of the foot and lower leg within the boot 10. Because of its foam construction, the shell 12 has a soft foam interior surface 14 that provides a high friction interface with the individual's skin. The interior surface 14 of the shell 12 is preferably smooth, though alternatively the surface 14 could be convoluted, having a pattern of peaks and valleys. Commercially available foam materials having this type of surface are known as convoluted foam or egg crate foam. In combination with the closure system (described in greater detail below), the soft foam interior surface 14 is adapted to inhibit and preferably prevent sliding of the lower leg within the boot 10.

Figure 7:
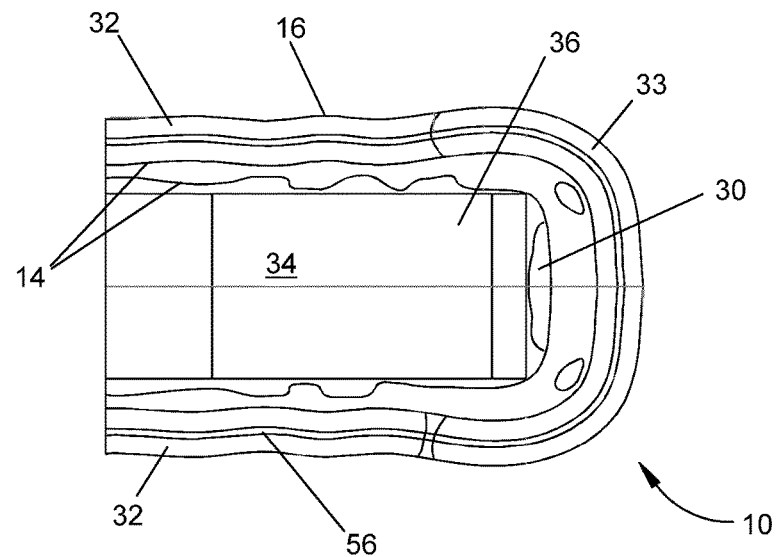

The interior surface 14 of the shell 12 defines a continuous cavity 34 within the boot 10 that is sized and shaped to receive the foot and lower leg of an individual. The interior surface 14 is separated from an exterior surface 16 of the shell 12 by a continuous rim 56 that completely borders an anterior opening 36 to the cavity 34, as seen in FIG. 7. In contrast to the high-friction interior surface 14, the exterior surface 16 of the boot 10 is preferably entirely covered with one or more low friction cover materials 18 (FIGS. 1, 2 and 3). As used herein, "low friction" means that the cover materials 18 provide a surface that results in the exterior of the boot having a lower friction than would be the case in the absence of the cover materials 18, and also lower than the interior surface 14 of the boot 10. In combination with the higher-friction interior surface 14 within the boot 10, the lower-friction exterior surface 16 of the boot 10 permits motion of the boot 10 relative to its surrounding environment, for example, bed coverings beneath and placed over the boot while the wearer is in bed, while simultaneously inhibiting motion of the individual's foot and ankle within the boot 10, thereby reducing the likelihood of unintended displacement of the foot within the boot 10. Other aspects of the cover materials 18 will be discussed in more detail below.

As most readily apparent in FIGS. 1, 2, 4 and 5, the shell 12 has a leg portion 24 adapted to support the lower leg and elevate the foot of an individual, and a forefoot portion 26 that supports the foot by applying supportive pressure to the foot sole for the purpose of preventing foot-drop (and equinus contractures). Because the boot 10 is similarly constructed and configured in accordance with Drennan, it shares many similar advantages and benefits. However, the boot 10 further improves over the teachings of Drennan by having a construction capable of increasing the support and comfort to the wearer.

With further reference to FIGS. 1 through 7, the shell 12 can be generally described as having oppositely-disposed anterior and posterior regions, with these terms being used in reference to the orientation of the boot 10 when worn by a person when in a supine position. The leg portion 24 defines oppositely-disposed lateral regions 32 (FIGS. 4 through 7), the forefoot portion 26 defines oppositely-disposed lateral regions 33 (FIGS. 6 and 7), and together the leg and forefoot portions 24 and 26 define the continuous cavity 34 (FIGS. 2 and 7) within the boot 10. The anterior opening 36 to the cavity 34 (FIG. 7) is defined by and between the lateral regions 32 and 33, and is sized to permit an individual's foot and lower leg to be lowered therethrough into the cavity 34. By comparing FIGS. 4 and 5, it can be seen that the right lateral region 32 of the leg portion 24 is sized larger than the opposing left lateral region 32, such that the right lateral region 32 is able to be folded onto and cover at least part and more preferably the entire anterior portion of an individual's lower leg received within the cavity 34.

As noted above, the preferred embodiment of the boot 10 shown in the Figures incorporates a closure system that facilitates tightening and adjustment of the boot 10 on an individual's lower leg. More particularly, the shell 12 is preferably secured to the lower leg and foot with straps 38 and 42 adapted to traverse the anterior opening 36 of the shell 12. While the closure system is illustrated as being exclusively achieved with straps 38 and 42, it is foreseeable that other types of closures could be utilized if capable of providing the adjustability of the straps 38 and 42 as described below.

Figure 4:
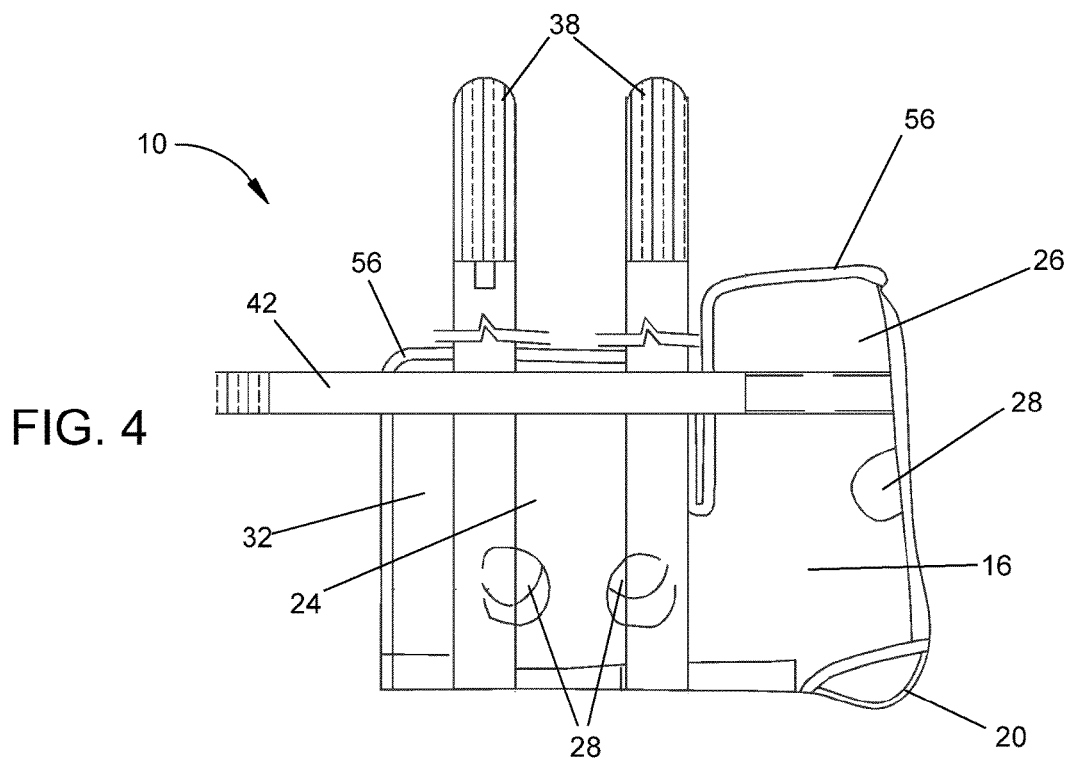
FIGS. 4 and 5 are, respectively, right and left side views of the protective boot shown in FIG. 1.
Figure 5:
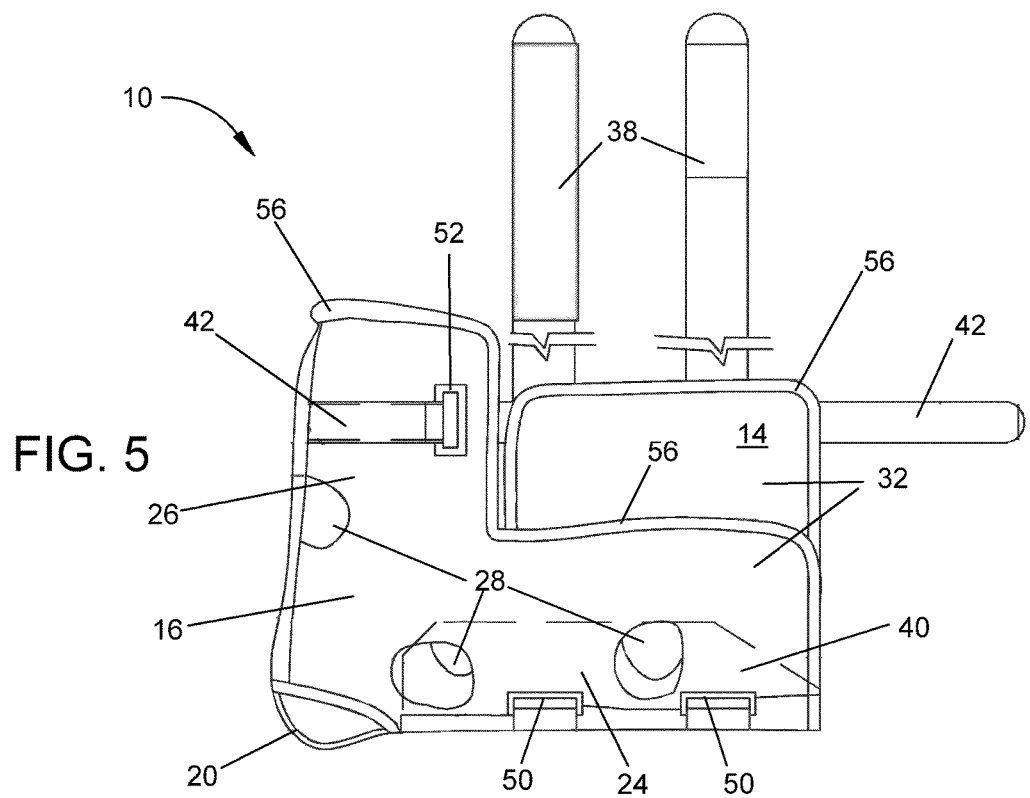
Figure 6:
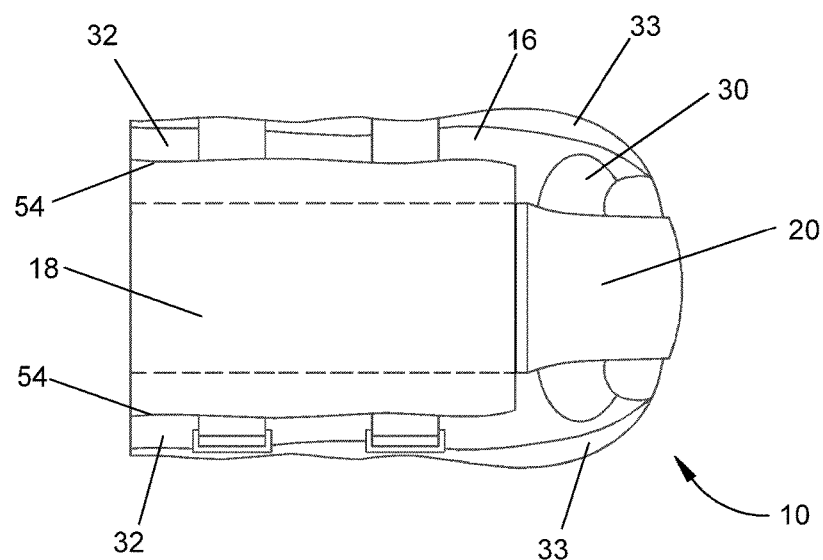
FIGS. 6 and 7 are, respectively, bottom and top views of the protective boot shown in FIG. 1.

The boot 10 preferably makes use of two leg straps 38, each working in cooperation with a buckle 50 attached to one of the lateral regions 32 of the leg portion 24. Each strap 38 may be attached to the lateral region 32 opposite its buckle 50 (e.g., the right lateral region 32 in the Figures), or optionally attached on the same lateral region 32 near the attachment point of its corresponding buckle 50 (e.g., the left lateral region 32 in the Figures). In use, the straps 38 are passed over the anterior opening 36 of the shell 12 toward their respective buckles 50, which provide generally D-shaped rings or slots through which the straps 38 can be inserted and then drawn back on themselves, allowing each strap 38 to be secured to itself with a suitable fastener, such as a complementary hook and loop closure material. As depicted in the Figures, the buckles 50 are preferably attached to the smaller lateral region 32 located on the left side of the boot 10, so that the larger lateral region 32 on the right side of the boot 10 is drawn down over the leg as the straps 38 are passed over the anterior opening 36 toward the buckles 50. By inserting the straps 38 in the buckles 50 and then drawing the straps 38 back onto themselves, the larger lateral region 32 is drawn snug over the individual's lower leg, as can be appreciated from FIG. 1. The strength of the attachment of the buckles 50 to the shell 12 can be promoted by attaching the buckles 50 with straps held with stitch lines 54 (FIG. 6). The attachment of the buckles 50 with short straps is believed to be preferable over rigidly attaching the buckles 50 to the shell 12 to allow some mobility of the buckles 50 for easier use and to avoid the possibility of a rigid connection causing pressure and discomfort to the individual.

The foot strap 42 and a corresponding buckle 52 are attached with two stitched lines 55 on the exterior surface 16 of the forefoot portion 26. The foot strap 42 is adapted to adjustably narrow the anterior opening 36 within the forefoot portion 26, enabling the forefoot portion 26 of the boot 12 to be tightened about the foot. The forefoot portion 26 and its lateral regions 33 and strap 42 are preferably configured so that the foot strap 42 does not cause the lateral regions 33 to completely close the anterior opening 36 within the forefoot portion 26, but instead draws the lateral regions 33 inward toward and into contact with the medial and lateral sides of the foot so that the lateral regions 33 of the forefoot portion 26 support the foot without applying pressure to the dorsum of the foot. As a result, the forefoot portion 26 of the boot 10 is able to remain close to the foot as it moves, and helps prevent rotation and shifting of the foot in the boot 10. Tightening the strap 42 about the forefoot portion 26 further reduces the likelihood that the boot 10 will catch on obstacles such as bed coverings, bed rails, wheelchairs, etc. The construction and operation of the foot strap 42 may be similar to the legs straps 38. In use, the strap 42 may be passed over the anterior opening 36 of the shell 12 toward the buckle 52. As with the buckles 50 of the straps 38, the buckle 52 may be a generally D-shaped ring or slot through which the strap 42 can be inserted and then drawn back on itself, allowing the strap 42 to be secured to itself with a suitable fastener, such as a complementary hook and loop closure material.

The buckles 50 and 52 serve as fulcrums for the straps 38 and 42, allowing the wearer or a caregiver to insert and properly tension each strap 38 and 42 with a single hand. This aspect frees up the second hand of the individual, which can then be used to balance the individual in bed while inserting or adjusting the straps 38 and 42. If a caregiver is performing this task, one hand of the caregiver is free to position and stabilize the individual's leg and foot within the boot 10. In either scenario, a proper amount of tension can be applied with the straps 38 and 42 with one hand while also ensuring proper positioning of the leg within the boot 10.

The boot 10 further comprises a cushion 40 (FIG. 2) within the shell cavity 34 for further elevating the lower leg (calf) and supporting the foot and lower leg without applying any support pressure at the heel of an individual's foot, thereby avoiding pressure sores at the heel. As depicted in FIG. 2, the cushion 40 is preferably a separable and adjustable cushion 40, though a cushion 40 that is integral with the shell 12 is also within the scope of the invention. The cushion 40 is further represented as having a bevel 44 at its upper distal edge. The combination of the cushion 40, its bevel 44, and a firmer forefoot portion 26 (due to the foot strap 42) is believed to improve the ability of the boot 10 to keep the heel elevated without undue pressure on the Achilles (calcaneal) tendon. Furthermore, the proximal end of the cushion 40 preferably has a bevel 46 (for example, 25 degrees) to reduce pressure on the calf. A suitable material for the cushion 40 is a foam material, preferably a "memory" foam or another type of polyurethane foam similar to that described for the shell 12, though it is foreseeable that other materials could be used. In certain preferred embodiments, the cushion 40 is capable of being heated and sterilized in an autoclave or oven with limited shrinkage. The cushion 40 can be permanently secured with an adhesive to the interior surface 14 of the cavity 34 within the leg portion 24 of the boot 10. Alternatively, the cushion 40 could be releasably secured with, for example, complementary fasteners of the hook-and-loop type to enable removal of the cushion 40 from the boot 10 as well as permit repositioning of the cushion 40 within the boot 10. Portions of the cushion 40 may be removed by the user, to accommodate Achilles tendon and/or malleolar decubitus injuries. In addition, the separate cushion 40 may be used to prevent boot and hip rotation by strapping the separate cushion 40 to the boot 10, either within the cavity 34 or at the exterior surface 16 of the boot 10 alongside one of the lateral portions 32.

Figure 8:
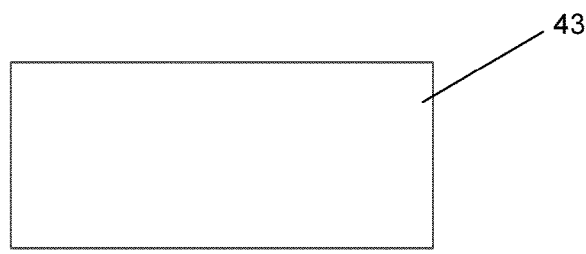
FIG. 8 represents an insert adapted for use with the protective boot of FIG. 1.

The boot 10 may further comprise an additional cushion or pad 43 (FIG. 8) that can be sized for temporary or permanent placement within the cavity 34 between the forefoot portion 26 and the individual's foot so that the pad 43 contacts the sole of the foot to provide additional support to the foot. Alternatively or in addition, the pad 43 can be sized for temporary or permanent placement within the cavity 34 beneath the individual's lower leg, or placed externally adjacent one of the lateral regions 32 of the boot 10 to control external rotation of the boot 10. As with the cushion 40 within the boot cavity 34, any additional pad 43 can be permanently or releasably attached to the lateral regions 32 of the boot 10 with adhesive, hook-and-loop fasteners, etc.

The leg and forefoot portions 24 and 26 of the shell 12 are preferably formed to have ventilation holes 28 that help to improve the comfort of the individual when the boot 10 is worn for long periods, though these holes 28 could be eliminated for some applications. The boot 10 preferably has a heel through-hole 30 at the intersection of the lower and forefoot portions 24 and 26 of the shell 12 in order to reduce the likelihood that any portion of the boot 10 will contact the individual's heel. The heel through-hole 30 is preferably sufficiently small to prevent the heel from passing therethrough.

As best seen in FIG. 2, certain embodiments of the boot 10 may include a stiffener 22 (FIG. 2) incorporated into the leg portion 24 or attached to its posterior surface to minimize buckling of the leg portion 24. A similar stiffener is disclosed in U.S. Pat. Nos. 5,449,339 and 7,458,948 to Drennan, whose contents relating to a stiffener are incorporated herein by reference. The stiffener 22 can be held in place with stitching, and may share the stitch lines 54 that attach the buckles 50 for the leg straps 38. Suitable materials for the stiffener 22 include polyethylene or polypropylene, though other materials could foreseeably be used. Preferred materials for the stiffener 22 are capable of being heated and sterilized in an autoclave or oven with limited shrinkage.

The one or more low-friction cover materials 18 that directly cover the exterior surface 16 of the shell 12 can be a laminate material, for example, a synthetic fabric polyester, such that these cover materials 18 define an exterior laminate permanently bonded to those portions of the shell's exterior surface 16 to which the cover materials 18 can be directly laminated, in other words, excluding the cover materials 18 that cover the backplate 20. The use of a laminated synthetic fabric polyester as the cover materials 18 can also be advantageous by providing better heat dissipation to improve comfort for the wearer. Preferably, the low-friction cover materials 18 are also chosen based on their ability to not fray or unravel/run with use (for example, some nylons tend to have these shortcomings), as well as being capable of being heated and sterilized in an autoclave or oven with limited shrinkage. The laminated low-friction cover materials 18 are intended to reduce the friction of the shell 12 to markedly reduce bed sheet friction, adding ease to mobility of the wearer's foot under bed coverings. The cover materials 18 may further comprise or be coated with a chemical to prevent staining. For example, chemical coatings are commercially available that enable liquids to roll off the material rather than being absorbed.

The interior surface 14 of the shell 12 within the cavity 34 may also be covered or laminated with a lining (not shown) to provide a cooler, drier environment for skin, as long as the interior surface 14 is a higher-friction surface than the exterior surface 16. Suitable linings for the interior surface 14 are preferably textured, high-friction, breathable, easy to clean, and antimicrobial, as well as capable of being heated and sterilized in an autoclave or oven with limited shrinkage. Commercial examples of suitable interior lining materials include CoolMax® or Outlast®. To maintain proper ventilation of the cavity 34, the ventilation holes 28 should remain uncovered by the cover materials 18 on the exterior surface 16 of the shell 12, as well as any lining on the interior surface 14. Lamination of the shell 12 allows for frequent washing and autoclaving sterilization.

According to another aspect of the present invention, the entire continuous rim 56 of the boot 10 surrounding the anterior opening 36, including the lateral portions 32 and 33 of the leg and forefoot portions 24 and 26, is formed with a low-friction fabric trim that is sewn onto the body 12 so as to form the rim 56 by compressing and narrowing the foam material along the entire perimeter of the anterior opening 36, as represented in FIGS. 2, 4, 5, and 7. The fabric trim serves to reinforce the foam material at the rim 56 to avoid tearing, and also compresses the foam material at the rim 56 to decrease its bulk and preferably define a smoother rim surface that further reduces friction and the risk of catching on bed coverings. While the trim may be an entirely separate material from the low-friction cover materials 18 that may be used to cover the exterior surface 16 of the boot 10, it is also foreseeable that the trim could be an integral portion of one or more of the cover materials 18.

From the foregoing, it should be appreciated that the boot 10 provides several advantageous structural adaptations. The forefoot portion 26 is sized and configured to provide greater and firmer support to the wearer, particularly when the foot strap 42 is used in combination with the additional pad 43 placed between the foot and forefoot portion 26. In addition, the cushion 40 and the bevels 44 and 46 at its distal and proximal ends provide greater support for the wearer's lower leg without undue pressure on the calf and Achilles (calcaneal) tendon. Finally, the low-friction cover materials 18 and rim 56 located on the exterior of the boot 10 and the higher-friction interior surface 14 within the boot cavity 34 cooperate to immobilize the wearer's foot and lower leg within the boot 10 while reducing friction between the boot 10 and its surrounding environment, for example, bed coverings beneath and placed over the boot 10 while the wearer is in bed.

The boot 10 described above can optionally further incorporate a backplate 20 in addition to or in lieu of the stiffener 22. As particularly evident from FIG. 2, the backplate 20 is located at both the posterior external surface 16 of the leg portion 24 and the distal exterior surface 16 of the forefoot portion 26 to minimize buckling of the boot 10 within the leg and forefoot portions 24 and 26. The backplate 20 is shown in FIG. 2 as being a single continuous L-shaped piece that extends from the proximal end of the leg portion 24 defined by a proximal portion of the continuous rim 56, and continues to a region of the forefoot portion 26 near a portion of the rim 56 surrounding the anterior opening 36 at the forefoot portion 26, thereby defining a posterior/calf portion, heel portion, and forefoot portion corresponding to, respectively, the lower leg portion 24, heel, and forefoot portion 26 of the shell 12. The backplate 20 is also shown as enclosed at the leg and forefoot portions 24 and 26, with the exception of its heel portion at the intersection of its posterior/calf and forefoot portions. Similar to the stiffener 22, suitable materials for the backplate 20 are capable of being heated and sterilized in an autoclave or oven with limited shrinkage. While polyethylene or polypropylene have suitable properties and can be used, the use of other materials is also within the scope of the invention.

With the inclusion of the backplate 20, the boot 10 can be additionally or alternatively utilized as an ankle-foot orthosis (AFO; brace) capable of providing support to an individual's ankle and forefoot, and may help to support weak/absent ankle dorsiflexors and prevent and/or correct plantarflexion deformity at the ankle. Preferred but nonlimiting features include the capability of redistributing pressure from wearer's heel to the calf and allowing both mobility and weight bearing (weight bearing ambulation). For the purpose of providing these capabilities, the backplate 20 is preferably sufficiently rigid to allow less than ten degrees of forefoot plantar motion, such that the backplate 20 determines the degree to which the wearer's lower leg, ankle and foot are able to more relative to each other. The foot strap 42 securing the wearer's ankle and foot to the backplate 20 facilitates weight-bearing ambulation. In particular, because the foot strap 42 draws the sides of the forefoot portions 33 inward toward and into contact with the sides of the wearer's foot to support the foot, the forefoot portion 26 of the boot 10 remains close to the foot as the wearer walks and helps prevent rotation and shifting of the foot in the boot 10.

The posterior/calf portion of the backplate 20 is preferably flat with proximal rounded corners. The posterior/calf portion is flat to limit rotation of the wearer's leg when the wearer is lying on their back. The heel portion of the backplate 20 spans the heel through-hole 30 of the shell 12 and is posteriorly curved and rounded, but substantially flat in the lateral (side to side) directions similar to the posterior/calf portion of the backplate 20. The heel portion transitions to the forefoot portion of the backplate 20, at which point the backplate 20 is no longer preferably flat, but instead has a side-to-side curvature. Notably, FIG. 2 shows the posterior/calf and forefoot portions of the foam shell 12 extending partially over a heel recess defined by the heel portion of the backplate 20, thereby reducing the likelihood that the wearer's heel would contact the backplate 20 through the heel through-hole 30 in the foam shell 12. As evident from FIG. 3, the backplate 20 can be considerably narrower (laterally) than the lower leg and forefoot portions 24 and 26 of the foam shell 12 to which it is attached. This lateral extension of the foam shell 12 protects the wearer's other limb from injury by giving the backplate 20 considerable padding protection.

As noted above, the backplate 20 is held in place on the lower leg and forefoot portions 24 and 26 of the shell 12 as a result of its posterior/calf and forefoot portions being enclosed with cover materials 18. The enclosed portions of the backplate 20 may be covered with the same low-friction cover materials 18 used to cover the exterior surface 16 of the boot 10, though it is foreseeable that different low-friction materials could be used for this purpose. For example, the backplate 20 may be held in place on the lower leg portion 24 of the foam shell 12 by a low-friction tricot material, whereas the backplate 20 may be held in place on the forefoot portion 26 of the foam shell by a heavier-duty higher-friction weight-bearing fabric material. The cover material(s) 18 can be secured with a stitch, which in FIGS. 3 and 6 is represented as part of the same stitch lines 54 and 55 that secure the buckles 50 and 52 of the strapping system. In view of the desired low-friction characteristics of the cover materials 18, FIGS. 1 and 3 further show a chevron pattern 58 disposed on the cover material 18 at the distal exterior surface 16 of the forefoot portion 26 and formed of a polymeric or other traction-promoting material.

While the invention has been described in terms of a specific embodiment, it is apparent that other forms could be adopted by one skilled in the art. For example, the boot 10 could differ in appearance and construction from the embodiment shown in the Figures, the functions of each component of the boot 10 could be performed by components of different construction but capable of a similar (though not necessarily equivalent) function, and appropriate materials could be substituted for those noted. Accordingly, it should be understood that the invention is not limited to the specific embodiment illustrated in the Figures. It should also be understood that the phraseology and terminology employed above are for the purpose of disclosing the illustrated embodiment, and do not necessarily serve as limitations to the scope of the invention. Therefore, the scope of the invention is to be limited only by the following claims.

The invention claimed is:

1. A protective boot for use by a person lying in a supine position and supporting a lower leg, heel, and foot thereof, the boot comprising:
    a body formed of a flexible and compressible foam material, the body having a proximal leg portion, a distal forefoot portion contiguous with and projecting from the leg portion in a transverse direction thereto, a continuous cavity defined by and within the leg and forefoot portions and being complementary in size and shape to support the lower leg of the person while supporting the foot of the person in an upright position, an anterior opening defined in the leg and forefoot portions to permit the foot and lower leg to pass therethrough into the cavity within the leg and forefoot portions, oppositely-disposed lateral regions defined by the leg portion and separated by the anterior opening, oppositely-disposed lateral regions defined by the forefoot portion and separated by the anterior opening, an interior surface defined by the leg and forefoot portions within the cavity, an exterior surface defined by the leg and forefoot portions, and a continuous rim separating the interior and exterior surfaces;
    a cushion within the cavity within the lower leg portion for supporting the lower leg of the person and suspending the heel of the person within the cavity;
    a first low-friction material defining the exterior surface at the leg and forefoot portions;
    a trim being a second low friction fabric at the continuous rim separating the interior and exterior surfaces, the second low-friction fabric trim being a different material than the first low-friction material defining the exterior surface of the body and being sewn onto the body so as to form the continuous rim in its entirety by compressing and narrowing the foam material of the body along the entire perimeter of the anterior opening;
    first means for adjustably closing the anterior opening in the leg portion with the lateral regions of the leg portion; and
    second means for adjustably closing a portion of the anterior opening in the forefoot portion with the lateral regions of the forefoot portion by drawing the lateral regions of the forefoot portion inward and toward the medial and lateral sides of the foot of the person within the forefoot portion without applying pressure to the dorsum of the foot.

2. The protective boot according to claim 1, wherein the body is a unitary, one-piece body formed of the flexible and compressible foam material.

3. The protective boot according to claim 1, wherein the first low-friction material entirely covers the exterior surface of the body.

4. The protective boot according to claim 1, wherein the first low-friction material is a cover laminated to the exterior surface of the body.

5. The protective boot according to claim 1, wherein the second low-friction fabric trim entirely covers the continuous rim.

6. The protective boot according to claim 1, wherein the cushion has a bevel on a distal end thereof.

7. The protective boot according to claim 1, wherein the cushion has a bevel on a proximal end thereof.

8. The protective boot according to claim 1, wherein the entirety of the protective boot is formed from materials capable of being heated and sterilized.

9. The protective boot according to claim 1, wherein the second closing means comprises a strap secured to the exterior surface at the forefoot portion.

10. The protective boot according to claim 1, further comprising a pad configured for placement within the cavity and between the foot of the person and the forefoot portion of the body.

11. The protective boot according to claim 1, further comprising an L-shaped backplate located at the leg and forefoot portions of the body and adapted to inhibit buckling of the boot within the leg and forefoot portions.

12. The protective boot according to claim 11, wherein the first low-friction material entirely covers a portion of the backplate located at the leg portion of the body.

13. The protective boot according to claim 12, wherein the first low-friction material entirely covers a portion of the backplate located at the forefoot portion of the body.

14. The protective boot according to claim 13, wherein the first low-friction material does not cover a portion of the backplate located between the leg and forefoot portions of the body.

15. The protective boot according to claim 14, further comprising a through-hole in the body that is spanned by the portion of the backplate located between the leg and forefoot portions of the body.

16. A protective boot for use by a person lying in a supine position and supporting a lower leg, heel, and foot thereof, the boot comprising:
    a unitary, one-piece body formed of a flexible and compressible foam material, the body having a proximal leg portion, a distal forefoot portion contiguous with and projecting from the leg portion in a transverse direction thereto, a continuous cavity defined by and within the leg and forefoot portions and being complementary in size and shape to support the lower leg of the person while supporting the foot of the person in an upright position, an anterior opening defined in the leg and forefoot portions to permit the foot and lower leg to pass therethrough into the cavity within the leg and forefoot portions, oppositely-disposed lateral regions defined by the leg portion and separated by the anterior opening, oppositely-disposed lateral regions defined by the forefoot portion and separated by the anterior opening, an interior surface defined by the leg and forefoot portions within the cavity, an exterior surface defined by the leg and forefoot portions, and a continuous rim separating the interior and exterior surfaces;

an L-shaped backplate having posterior and forefoot portions located at, respectively, the leg and forefoot portions of the body and a heel portion located between the posterior and forefoot portions of the backplate, the backplate being adapted to inhibit buckling of the boot within the leg and forefoot portions, wherein the leg and forefoot portions of the body extend at least partially over a heel recess defined by the heel portion so as to be spaced apart from the heel portion and reduce the likelihood that the heel of a person wearing the boot will contact the backplate within the heel recess;

a low-friction fabric trim being a different material than the exterior surface of the body and being sewn onto the body so as to form and cover the continuous rim in its entirety by compressing and narrowing the foam material of the body along the entire perimeter of the anterior opening;

a separable adjustable cushion within the cavity within the lower leg portion for supporting the lower leg of the person and suspending the heel of the person within the cavity; and first means for adjustably closing the anterior opening in the leg portion with the lateral regions of the leg portion.

17. The protective boot according to claim 16, further comprising a pad configured for placement within the cavity between the foot of the person and the forefoot portion of the body.

18. The protective boot according to claim 16, the protective boot further comprising a through-hole in the body that is spanned by the portion of the backplate located between the leg and forefoot portions of the body.

19. The protective boot according to claim 18, further comprising:
a low-friction cover material laminated to and entirely covering the exterior surface of the body, covering portions of the backplate located at the leg and forefoot portions, and not covering a portion of the backplate located between the leg and forefoot portions of the body; and second means for adjustably closing a portion of the anterior opening in the forefoot portion with the lateral regions of the forefoot portion by drawing the lateral regions of the forefoot portion inward and toward the medial and lateral sides of the foot of the person within the forefoot portion without applying pressure to the dorsum of the foot.

20. The protective boot according to claim 19, wherein the first and second closing means comprise straps secured to the exterior surface at the leg and forefoot portions of the body.

* * * * *